United States Patent [19]

Takishita et al.

[11] Patent Number: 4,768,155

[45] Date of Patent: Aug. 30, 1988

[54] SUPERSONIC FLAW DETECTING SYSTEM

[75] Inventors: Yoshihiko Takishita; Toshio Nonaka; Yasuo Hayakawa, all of Ibaraki, Japan

[73] Assignee: Hitachi Construction Machinery Co., Ltd., Tokyo, Japan

[21] Appl. No.: 820,607

[22] Filed: Jan. 21, 1986

[30] Foreign Application Priority Data

Jan. 19, 1985 [JP] Japan ................................ 60-6702

[51] Int. Cl.$^4$ .............................................. G01N 9/24
[52] U.S. Cl. ..................................... 364/507; 73/618; 73/634
[58] Field of Search ............... 364/507, 508, 506, 552, 364/490, 525, 414; 73/620, 632, 633, 634, 607, 618, 621; 340/731; 128/660; 358/112

[56] References Cited

U.S. PATENT DOCUMENTS

| | | | |
|---|---|---|---|
| 3,996,792 | 12/1976 | Kubota et al. | 364/507 |
| 4,098,130 | 7/1978 | Coffey et al. | 364/507 |
| 4,213,183 | 7/1980 | Barron et al. | 364/507 |
| 4,240,295 | 12/1980 | Uranishi | 73/607 |
| 4,353,257 | 10/1982 | Vrba et al. | 364/507 |
| 4,361,043 | 11/1982 | Engle | 73/620 |
| 4,470,303 | 9/1984 | O'Donnell | 73/633 |
| 4,472,972 | 9/1984 | Riley et al. | 73/620 |
| 4,475,394 | 10/1984 | Takeda et al. | 73/633 |
| 4,520,671 | 6/1985 | Hardin | 73/633 |
| 4,543,827 | 10/1985 | Tominaga et al. | 364/508 |
| 4,618,934 | 10/1986 | Nagase | 364/507 |
| 4,630,612 | 12/1986 | Uchida et al. | 128/660 |
| 4,671,292 | 6/1987 | Matzuk | 128/660 |

FOREIGN PATENT DOCUMENTS

| | | | |
|---|---|---|---|
| 2263177 | 11/1971 | Fed. Rep. of Germany | 73/620 |
| 2428254 | 6/1980 | France | 364/507 |

OTHER PUBLICATIONS

Pan et al., Ultrasonic Imaging System, International Application Number PCT/US85/01016 published under the Patent Cooperation Treaty, Dec. 19, 1985, Publication #WO85/05683.
Moyer & Gray, Expanding the Capability of a Laboratory Ultrasonic Test Facility, Oct. 1973, Materials Evaluation, pp. 193-198, 204.
Brase et al., An Automated Ultrasonic Test Bed, Materials Evaluation/42/Dec. 1984, pp. 1619-1625.

Primary Examiner—Parshotam S. Lall
Assistant Examiner—S. A. Melnick
Attorney, Agent, or Firm—Antonelli, Terry & Wands

[57] ABSTRACT

A supersonic flaw detecting system has a probe adapted to emit a supersonic wave towards an object to be inspected, a scanning device for causing a relative movement between the probe and the object in two orthogonal directions, a pulser-receiver adapted to supply pulses to the probe and receive the supersonic wave from the object and produce an electric signal indicative thereof, a signal processing device for converting the electric signal from the pulser-receiver into an image data signal for a C-scope display, an oscilloscope for conducting an A-scope display of the electric signal from the pulser-receiver, and a monitor T.V. having a screen for conducting the C-scope display of the image data signal from the signal processing device. A control unit when the probe and object are relatively moved by the scanning device, the image data carried by the image data signal from the signal processing device at a corresponding address in the image memory at each pitch which has been determined such that the number of data pickups during the relative movement between the probe and the object coincides with the number of the corresponding addresses in the image memory to thereby cause C-scope display of the image data to be effected on the screen. The is operative to compute, when the cursor is displayed on the screen by the operation device, the amount of operation of the scanning device necessary for locating the probe relative to the object at a position corresponding to the cursor on the screen and operate the scanning device by the thus computed amount to locate the probe at the corresponding position, thereby permitting A-scope display to be effected at such a position on the oscilloscope.

8 Claims, 11 Drawing Sheets

FIG. 2
(a) (b) (c) (d)
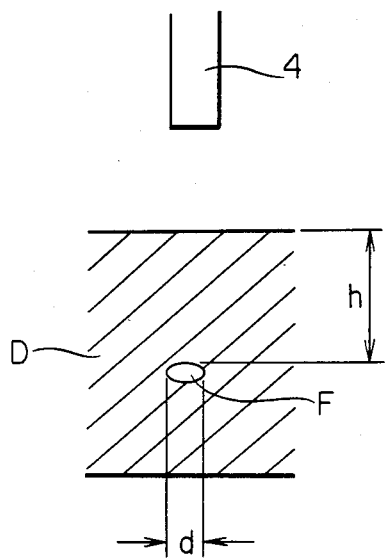
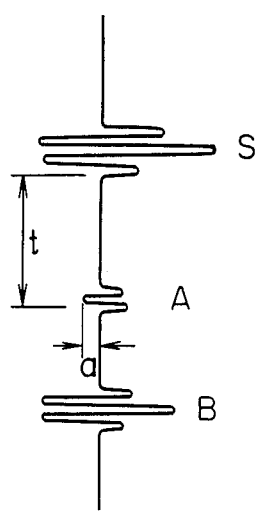
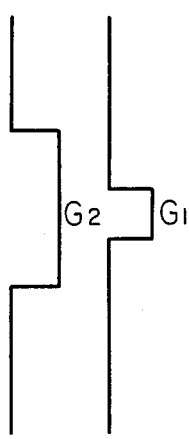

SUPERSONIC FLAW DETECTING SYSTEM

BACKGROUND OF THE INVENTION

The present invention relates to a supersonic flaw detecting system and, more particularly, to a supersonic flaw detecting system which is capable of successively conducting C-scope display and A-scope display and investigating any flaws in an object to be inspected from the both displays.

A supersonic flaw detecting system has been used for investigation of any internal flaw of an object such as a semiconductor, metal sheet and ceramics structure. The known supersonic flaw detecting system can be sorted into three types according to the type of display: namely, an A-scope display type, a B-scope display type and C-scope display type. The A-scope display type flaw detecting system has a probe which is energized to emit a supersonic wave towards an object, and an oscilloscope which displays waves reflected from the object, for example, with the axis of abscissa representing time and the axis of ordinate representing amplitudes of the waves, so as to permit surface echo reflected from the surface of the object, flaw echo reflected from the flaw and bottom echo reflected from the bottom surface of the object to be observed, so that the depth of the flaw from the object surface can be learned by measuring the time difference between the peaks of the surface echo and the flaw echo, and at the same time, the size of the flaw can be learned by reading the maximum or minimum amplitude of the flaw echo.

The B-scope display type flaw detecting system has a probe which scans the object only in one direction, and a monitor T.V. which displays the surface echo, flaw echo and bottom echo in terms of gradation according to the intensities of these echos, with the axis of abscissa representing the distance of movement of the probe and the axis of ordinate representing the depth (distance) in section of the object. The monitor T.V., therefore, can display the vertical section of the object including flaw information, so that the presence and the position of the flaw can be learned with a concept of area of a plan.

The C-scope display type flaw detecting system has a probe which scans the object both in vertical and horizontal directions, and a monitor T.V. which displays the flaw echo from a certain region of depth of the object determined by the gate width of a gate circuit, with the axis of abscissa and the axis of ordinate representing, respectively, the distances of the lateral (X direction) and longitudinal (Y direction) movements of the probe, in terms of gradation according to the intensity of the flaw echo. The monitor T.V., therefore, can display the cross-section of the object, including flaw information, so that the presence of the flow can be learned over the whole portion of the object.

A supersonic flaw detecting system has been also known which can conduct both the A-scope display and the C-scope display. In the use of this flaw detecting system, at first the presence, position and size of any flaw are roughly sounded by A-scope displays on a plurality of portions of the object and, thereafter, requirements for obtaining a clear C-scope display, such as gate width, amplifier gain of a pulse-receiver, focal position, i.e., the height of the probe (when the probe is of focus type) are determined in accordance with the A-scope information, and then the system is adjusted in accordance with the requirements and the C-scope display is conducted, thereby obtaining the detail of the flaw information over the entire portion of the object.

All the known flaw detecting system mentioned above, however, require laborious works with high degree of skill of an operator, as well as time, for obtaining exact flaw information over the entire portion of the object. Namely, the flaw detection by the A-scope type detecting system requires repetition of a considerably large number of A-scope displays for covering the entire area of the object, because each display provides only information of a portion just below the probe. In addition, since the previous information is extinguished from the oscilloscope, the operator has to compose the image of the flaws in the form of a line or a plane in his brain, which requires a high degree of skill and experience. The flaw detection by the B-scope type system also requires repetition of scanning and display operations as well as the brain work of an operator to provide flaw information in the form of a plane. The C-scope type detecting system permits the presence of any flaw to be investigated over the entire portion of the object, but cannot directly provide the exact information about the depth of the flaw. The exact depth information may be obtained by narrowing the gate width, but this causes a risk of exclusion of flaw echos from the depth other than the region corresponding to the narrowed gate width. Thus, in this case, the C-scope display has to be conducted on a plurality of depth regions in order to obtain flaw information over the full depth of the object. On the other hand, when the gate idth is widened, the disadvantage would occur that, when two or more flaws exist in an overlapping manner at different depths, the number of such flaws cannot be discriminated.

The flaw detecting system which conducts the A-scope display followed by the C-scope display also requires much time and labour because the initial A-scope display has to be conducted on a multiplicity of points until the presence of flaw is investigated over the entire portion of the object.

SUMMARY OF THE INVENTION

Accordingly, an object of the invention is to provide a supersonic flaw detecting system which can simply and quickly provide flaw information such as presence or absence of flaw, flaw size and flaw position, thereby overcoming the above-described problems of the prior art.

To this end, according to the invention, there is provided a supersonic flaw detecting system having a probe adapted to emit a supersonic wave towards an object to be inspected, scanning means for causing a relative movement between said probe and said object in two orthogonal directions, a pulser-receiver adapted to supply pulses to said probe and receive the supersonic wave from said object and produce an electric signal indicative thereof, signal processing means for converting said electric signal from said pulser-receiver into an image data signal for a C-scope display, oscilloscope means for conducting an A-scope display of said electric signal from said pulser-receiver, and a monitor T.V., having a screen for conducting the C-scope display of said image data signal from said signal processing means, said supersonic flaw detector comprising: image memory means connected to said monitor T.V. and having addresses corresponding to the coordinate values of a coordinate system assumed on the screen of said monitor T.V.; operation means adapted to be operated by an operator for accessing a desired one of the addresses in said image memory means to display position indicating means on the screen of said monitor T.V. at a coordinate position corresponding to the accessed address; and control means connected to said scanning means, said signal processing means, said image memory means and said operation means, and operative to write, when said probe and object are relatively moved by said scanning means, the image data carried by said image data signal from said signal processing means at a corresponding address in the image memory means at each pitch which has been determined such that the number of data pickups during the relative movement between said probe and object coincides with the number of the corresponding addresses in said image memory means, to thereby cause C-scope display of the image data to be effected on the screen of said monitor T.V.; and to compute, when said position indicating means is displayed on said screen by said operation means, the amount of operation of said scanning means necessary for locating said probe relative to said object at a position corresponding to said position indicating means on the screen of said monitor T.V., from said pitch and the address in said image memory means accessed by said operation means, and operate said scanning means by the thus computed amount to locate said probe at said corresponding position, thereby permitting A-scope display to be effected at such a position on said oscilloscope means.

BRIEF DESCRIPTION OF THE DRAWINGS

FIGS. 2a to 2d are views of the manner in which the gate width is set in a gate circuit incorporated in the supersonic flaw detecting system shown in FIG. 1 wherein FIG. 2a is a sectional view of a probe and an object to be inspected, FIG. 2b shows waves reflected from the object in relation to the section of the object, and FIGS. 2c and and 2d are views of the gate widths of the gate circuit in relation to the reflected waves;

DESCRIPTION OF THE PREFERRED EMBODIMENTS

Figure 1:
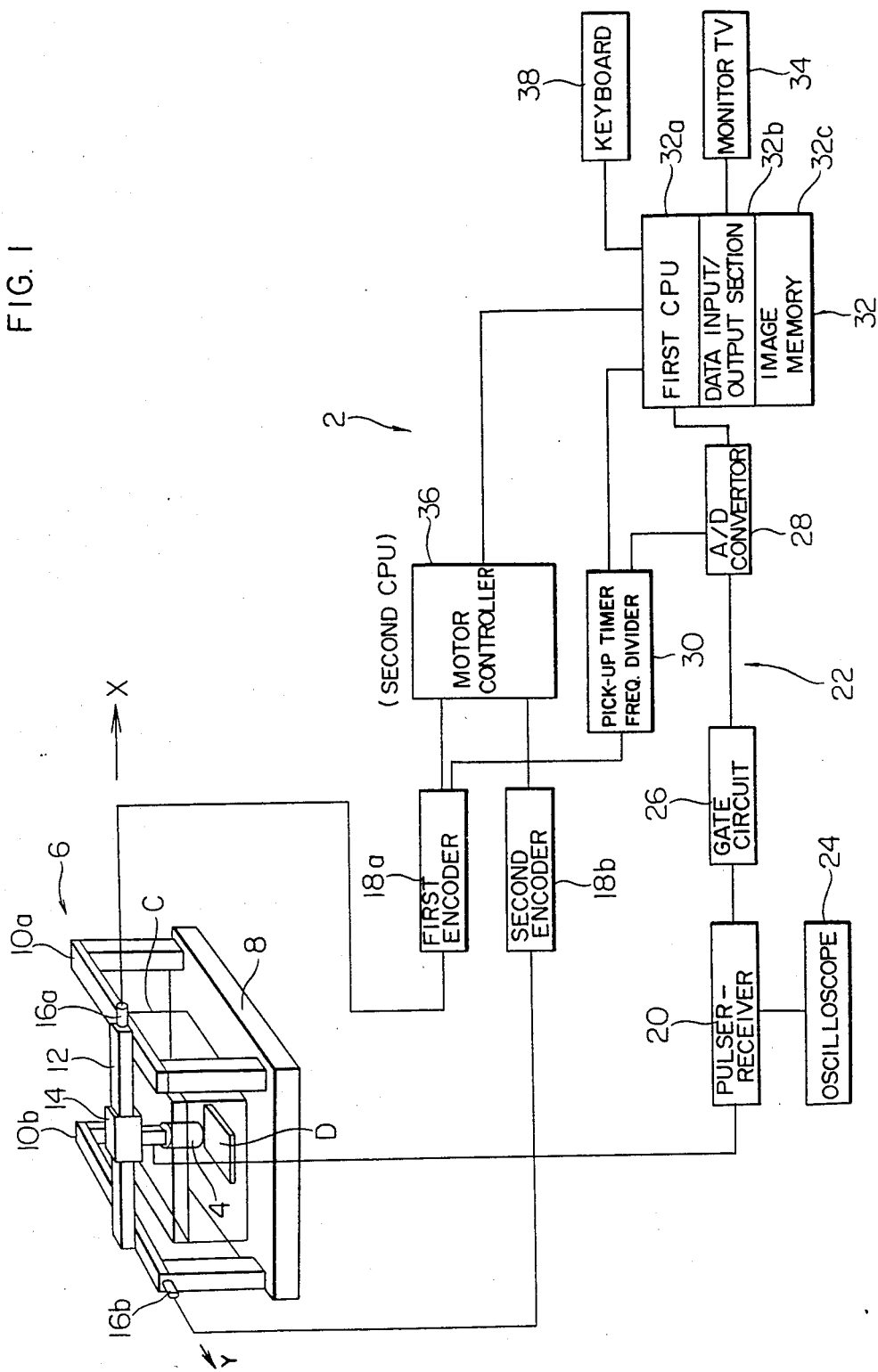
FIG. 1 is a schematic view of a preferred embodiment of a supersonic flaw detecting system according to the invention.
Figure 3:
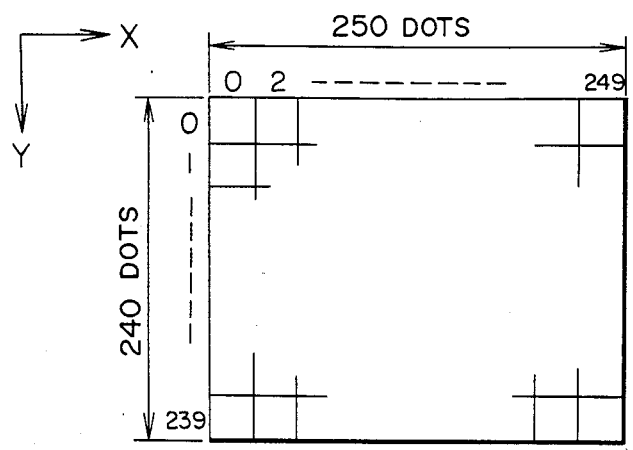
FIG. 3 is a view of the relationship between an X-Y coordinate system assumed on a monitor T.V. and addresses in an image memory.

Referring to FIG. 1, a preferred embodiment of a supersonic flaw detecting system in accordance with the invention is generally designated at a reference numeral 2. The system 2 has a probe 4 of, for example, focus type which is adapted to emit a supersonic wave of a frequency ranging between, for example, 2 MHz and several tens of MHz towards an object D to be inspected which is placed on the bottom of a container C filled with water. The probe 4 is adapted to be moved relative to the object D by a scanning device 6 in two orthogonal directions, namely, in X and Y directions. The probe 4 may be of flat type which emits a supersonic wave in a parallel direction. The container C is placed on a supporting plate 8 which is provided with a pair of parallel stationary guides 10a, 10b which extends in the Y direction. A movable guide 12 oriented in the X direction is movable in the Y direction with respect to the stationary guides. The movable guide carries a support 14 which supports the probe 4 and is movable in the X direction relative to the movable guide 12.

In the embodiment as shown, the scanning device 6 has, in addition to the stationary guides 10a, 10b, movable guide 12 and the support 14, a first motor 16a mounted on the movable guide 12, a second motor 16b mounted on one 10b of the stationary guides, and first and second encoders 18a, 18b connected to the first and second motors, respectively, and adapted to output the pulse signals of frequencies proportional to the amounts of rotation of the first and second motors. The operation of the first motor 16a causes, through a suitable mechanism such as rack-and-pinion (not shown), the support 14 to be moved in the X direction along the movable guide 12 so that the probe 4 can scan the object D in the X direction. Similarly, the operation of the second motor 16b causes, through a mechanism such as a rack-and-pinion (not shown), the movable guide 12 to be moved in the Y direction along the stationary guides 10a, 10b so that the probe 4 can scan the object D in the Y direction. The scanning device 6 may have the supporting plate 8 constructed as an X-Y stage so that the container C and the object therein can be moved in X and Y directions instead of moving the probe.

The probe 4 has a pulser-receiver 20 connected thereto and adapted to supply pulses to the probe to energize its oscillating element for emission of the supersonic wave and receive, through the probe 4, the wave reflected by the object and produce an electric signal indicative thereof. To the pulser-receiver 20 is connected a signal processing device 22 for converting the electric signal into an image data signal for C-scope display, and an oscilloscope 24 for A-scope display of the electric signal. The signal processing device 22 includes a gate circuit 26 which applies a gate to the electric signal from the pulser-receiver 20 and outputs a D.C. analog voltage proportional to the maximum value or minimum value (maximum negative value) of a waveform within the gate, and an A/D converter 28 connected to the gate circuit 26 and adapted to digitize the analog voltage and output the digital voltage as the image data signal.

The application of the gate in the gate circuit 26 is conducted in the following manner. Assuming that the object D has a flaw F of a size d at a depth h from the surface thereof, as shown in FIG. 2a, the A-scope display thereof will show signals as shown in FIG. 2b, in which the waveform includes a surface echo S reflected from the surface of the object D, a flaw echo A reflected from the flaw F and a bottom echo B reflected by the bottom surface of the object D. The time interval t between the surface echo S and the flaw echo A has a value proportional to the depth h of the flaw F, while the minimum amplitude a of the flaw echo A has a value proportional to the size d of the flaw F. Thus, it is possible to obtain information of the flaw F by detecting the values t and a. In the case the gate is applied to such a waveform, the width of the gate may be selected to be narrow as of a gate $G_1$ so as to cover only a narrow region where the flaw echo is expected to appear, as shown in FIG. 2d. However, such a narrow gate involves a risk of a flaw detection failure in the event that the flaw F is out of the gate, and in some cases, it is impossible to learn the depth(h) of the flaw F. In the embodiment as shown, therefore, the width of the gate is selected to be as large as possible as of a gate $G_2$ so as to provide a large margin without reaching the surface echo S and the bottom echo B, as shown in FIG. 2c. However, in the case where the depth of the flaw can be predicted with a high probability as in the case of inspection of the bonding between adjacent layers in a semiconductor, it is preferred that the width of the gate is reduced as is the case of the gate $G_1$ as shown in FIG. 2d. In such a case, a flaw echo of a clear waveform and, hence, a clear C-scope display of the flaw can be obtained by adjusting the water distance between the probe 4 and the object D such that the supersonic wave emitted from the probe 4 is accurately focussed on the bonding layer.

The A/D converter 28 is connected to a data pick-up timing device such as a frequency divider 30 adapted to output a trigger signal at a timing which will be explained later and conducts A/D conversion and outputs the image data signal only when it receives the trigger signal. The image data signal outputted from the A/D converter 28 is delivered to an image processing unit 32 and, after being processed by this unit, it is sent to a monitor T.V. 34 having a screen for C-scope display.

The image processing unit 32 has a first CPU 32a, an data input/output section 32b and an image memory 32c. The first CPU 32a is connected to the A/D converter 28 so as to receive the image data signal therefrom and is also connected to the frequency divider 30 so as to control the timing at which the frequency divider 30 outputs the trigger signal. The first CPU is also connected to a motor controller 36 incorporating a second CPU therein and to a keyboard 38 which provides an operation device operated by an operator. The frequency divider 30 is further connected to the first encoder 18a, while the motor controller 36 is connected to the first and second encoders 18a and 18b. The second CPU in the motor controller 36 may be integrated with the first CPU 32a such that the first CPU 32a also has the function of the second CPU. The data input/output section 32b is connected to the monitor T.V. 34. The image data signal received by the first CPU 32a is stored in the image memory 32c through the data input/output section 32b, and is outputted to the monitor T.V. 34 through same.

The image memory 32c has addresses corresponding to the coordinate values of a coordinate system assumed on the screen of the monitor T.V. 34. More specifically, assuming here that the coordinate system assumed on the screen of the monitor T.V. is an X-Y coordinate system having 250 dots in the X direction and 240 dots in the Y direction, for example, the coordinate value (Xa, Ya) varies between 0 and 249 with respect to the value Xa and between 0 and 239 with respect to the value Ya. Similarly, the address in the image memory 32c is expressed by the values (Xa, Ya) in which the value Xa varies between 0 and 249 and the value Ya varies between 0 and 239. When the address (Xa, Ya) is accessed, the image data carried by this address is displayed on the screen at the dot of the coordinate value (Xa, Ya) having the same values Xa and Ya as the address. In this manner, when all the addresses in the image memory 32c storing the image data are accessed, the whole image data are displayed on the screen of the monitor T.V. in the form of C-scope display.

The keyboard 38 is adapted to set and instruct the range of scanning of the probe 4 relative to the object D, and also to access a desired address (Xa, Ya) in the image memory 32c to display a position indicator such as a cursor at a corresponding coordinate portion on the screen of the monitor T.V. 34.

In the first CPU 32a, the number of data pickups corresponding to the number of X-coordinate values of the addresses (Xa, Ya) in the image memory 32c, i.e., 250 in this case, is set beforehand. The first CPU 32a is operative to divide the X direction distance of the scanning range instructed by the keyboard 38 by the number of data pickups to compute a pitch at which the image data are to be picked up when the probe 4 is moved relative to the object D by the scanning device 6. On the basis of the thus computed pitch, the first CPU 32a is further operative to compute the amount of operation of the scanning device 6 required for moving the probe 4 over the scanning range instructed by the keyboard 38, and in cooperation with the second CPU in the motor controller 36, operate the scanning device 6 in accordance with the computed amount, while controlling the timing of delivery of the trigger signal from the frequency divider 30 so as to coincide with the pitch. At the same time, the first CPU 32a receives the image data signal outputted from the A/D converter 28 in accordance with the trigger signal from the frequency divider 30 which is thus controlled and is operative to write the image data carried by the image data signal at a corresponding address (Xa, Ya) in the image memory 32c, to thereby cause C-scope display of the image data to be effected on the screen of the monitor T.V. 34. The first CPU 32a is further operative to access a desired address (Xa, Ya) in the image memory 32c by the operation of the keyboard 38 to display the cursor at a corresponding position on the screen of the monitor T.V. 34, while the second CPU in the motor controller 36 is operative to compute the amount of operation of the scanning device 6 required for locating the probe 4 at a position corresponding to the position of the cursor, from the value (Xa, Ya) of the accessed address and the pitch mentioned above, and operate the scanning device 6 in accordance with the computed amount to locate the probe 4 at the corresponding position, thereby permitting A-scope display to be effected at such a position by the oscilloscope 24.

A detailed description will be made hereinunder as to the function and operation of the first CPU 32a and the second CPU with reference to flow charts shown in FIGS. 4 to 9. The description will be made first as to the C-scope display by the monitor T.V. 34 with reference to FIGS. 4 to 7, and then as to the process for locating the probe 4 at the position corresponding to the cursor position for effecting A-scope display by the oscilloscope 24 with reference to FIGS. 8 and 9.

Function and Operation for C-Scope Display

Figure 4:
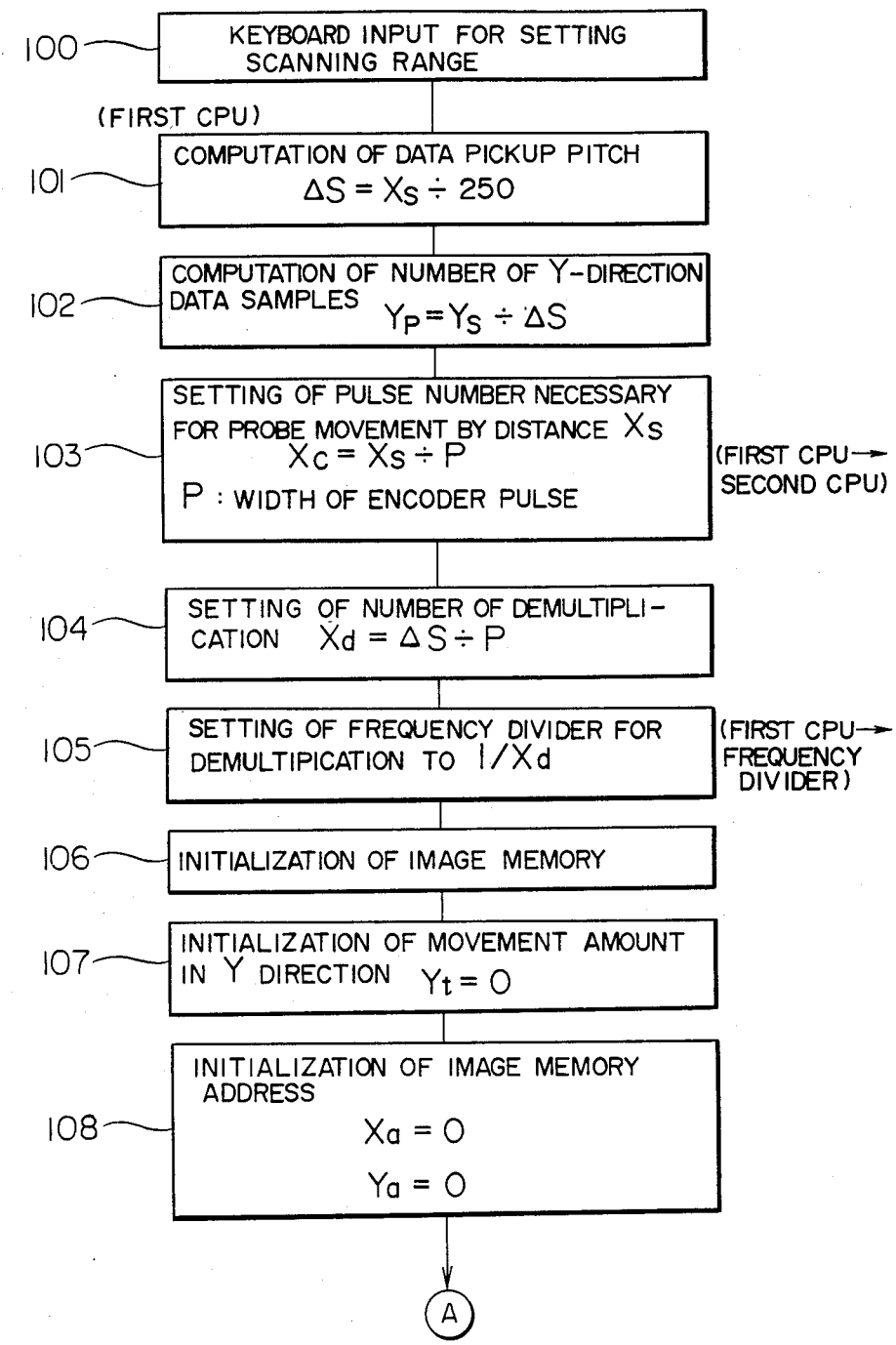
FIGS. 4 to 7 are flow charts showing procedures performed by first and second CPUs in the supersonic flaw detecting system shown in FIG. 1 to conduct C-scope display.
Figure 10:
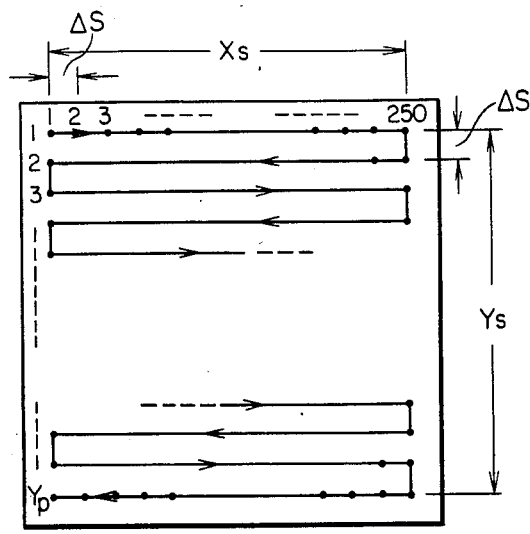
FIG. 10 is a view of the manner in hich the object is scanned by the probe.
Figure 11:
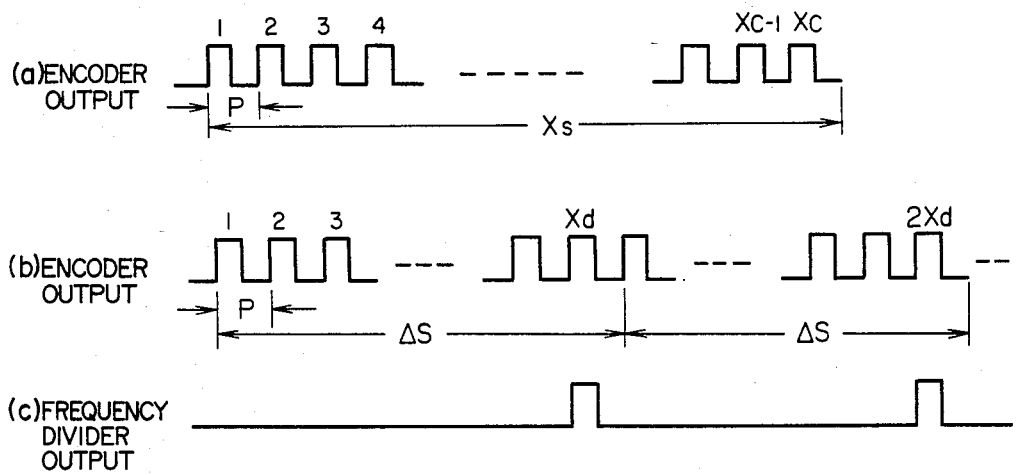
FIGS. 11a and 11b, respectively, are views of the relationship between the number of the output pulses from a first encoder and the distance of a set scanning range in the X direction and the relationships between the number of output pulses from the first encoder and the data pickup pitch
FIG. 11c is the output of a frequency divider.

Referring to FIG. 4, the keyboard 38 is operated to set and instruct the range of scanning of the probe 4. This is conducted by inputting the values of the X direction distance Xs and the Y direction distance Ys of the scanning range as shown in FIG. 4 (Step 100). As stated before, the number 250 corresponding to the number of the X coordinate values of the address (Xa, Ya) in the image memory 32 has been stored in the first CPU 32a as the number of data pickups. The first CPU 32a computes, in response to the instruction given by the keyboard 38, the data pickup pitch ΔS by dividing the X direction distance Xs of the scanning range by the number of data pickups, i.e., by 250 (Step 101). Then, the first CPU 32a computes the number Yp of Y direction data samples by dividing the Y direction distance Ys of the scanning range by the computed pitch ΔS (Step 102), and also computes the number Xc of pulses of the first encoder 18 necessary for moving the probe 4 by the X direction distance Xs of the set scanning range, by dividing the distance Xs by the pulse width P of the pulse of the first encoder 18 (Step 103). The relationship between the distance Xs and the pitch ΔS, as well as the relationship between the distance Ys, pitch ΔS and the number Yp are shown in FIG. 10, and the relationships between the distance Xs, pulse width P and the pulse number Xc are shown in FIG. 11. The first CPU 32a also computes the number Xd of demultiplication (the number of pulses) by dividing the pitch ΔS by the pulse width P of the pulse signal from the first encoder 18a (Step 104), and instructs the frequency divider 30 to set same for demultiplication to 1/Xd (Step 105). The relationships between the pitch ΔS, pulse width P and the pulse number Xd, as well as the relationships between these values and the output from the frequency divider 30 set for demultiplication to 1/Xd, are shown in FIG. 11b. Then, the first CPU 32a initializes the image memory 32c by erasing the data stored therein (Step 106), and then initializes the Y direction movement Yt by setting Yt =0 (Step 107), and initializes the address (Xa, Ya) in the image memory by setting Xa =0 and Ya =0 (Step 108).

Figure 5:
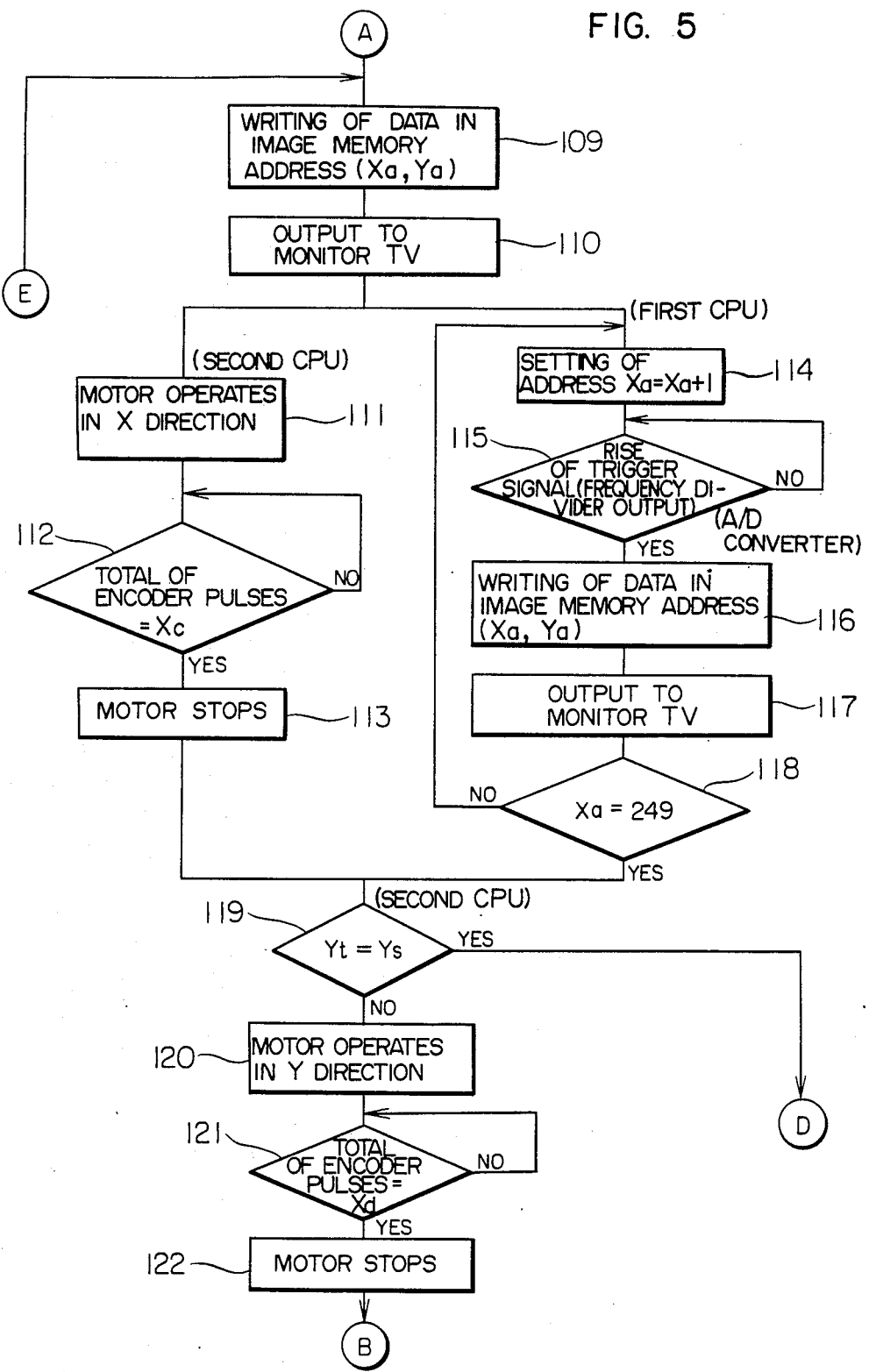

Subsequently, the pulser-receiver 20 is actuated to cause the probe 4 to emit a supersonic wave. In response to this operation, the first CPU 32a instructs the A/D converter 28 to deliver its output, so that the image data obtained with the probe 4 in the initial position is outputted from the A/D converter 28. As shown in FIG. 5, the first CPU 32a writes this data at the address (Xa, Ya) in the image memory 32c (Step 109), and the thus written data is immediately delivered from the image memory to the monitor T.V. (Step 110). Subsequently, the second CPU of the motor controller 36 operates the first motor 16a to cause the probe 4 to be moved in the X direction relative to the object D (Step 111), and judges whether or not the total of the pulses from the first encoder 18a has reached the value Xc computed in Step 103 (Step 112). When it is judged that this value has been reached, the second CPU operates to stop the first motor 16a (Step 113). At the same time, the first CPU 32a establishes a new X coordinate value of the address in the image memory 32c by setting Xa=Xa+1 (Step 114). The A/D converter 28 delivers the image data signal only when it receives the trigger signal from the frequency divider 30 (Step 115), and the first CPU 32a writes this image data at the address (Xa, Ya) in the image memory 32c (Step 116) and causes the image memory 32c to immediately output this data to the monitor T.V. 34 (Step 117). Then, the first CPU 32a makes judgement as to whether the X coordinate value Xa of the address has reached 249 (Step 118). If this value has not been reached, the steps 114 to 118 are conducted repeatedly, and the data pickup in the X direction by the steps 111 to 113 is completed when this value is reached.

Then, the second CPU makes a judgement as to whether the movement Yt of the probe 4 in the Y direction has reached the set value Ys (Step 119). When this value has not been reached, the second CPU operates the second motor 16b thereby moving the probe 4 in the Y direction (Step 120), and makes a judgement as to whether the total of pulses from the second encoder 18b has reached the pulse number Xd which has been determined in Step 104 for providing the pitch ΔS (Step 121). When this value is reached, the second CPU stops the second motor 16b (Step 122).

Figure 6:
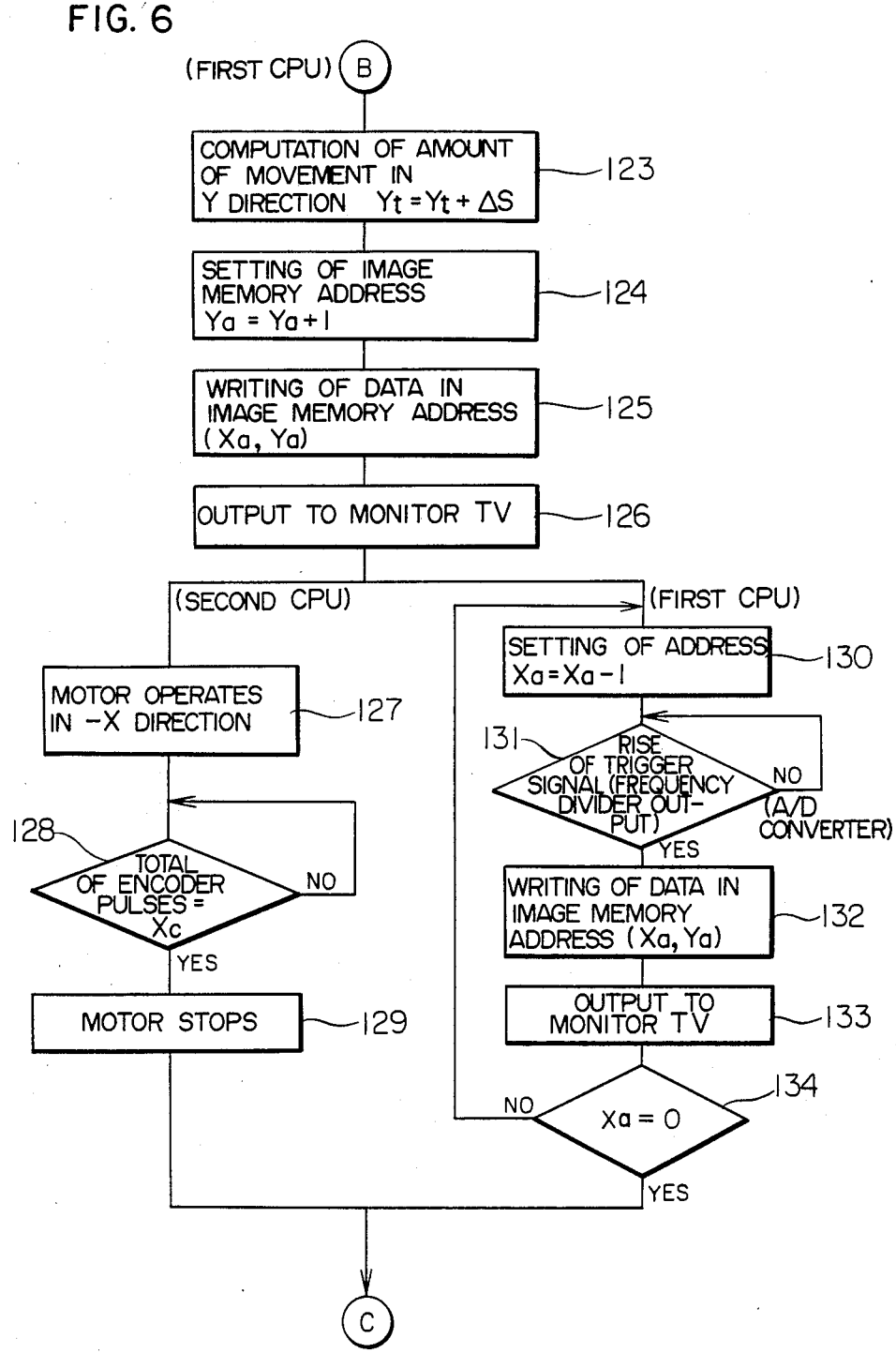

Referring now to FIG. 6, the amount of movement in the Y direction is computed by setting Yt =Yt +ΔS (Step 123), and the Y coordinate value of the address in the image memory 32c is set by conducting Ya =Ya +1 (Step 124). Then, a trigger signal is applied to the A/D converter 28 thereby causing the latter to output the image data signal as obtained when the second motor 16b has been stopped in the step 122, and writing the data at the address (Xa, Ya) in the image memory 32c (Step 125). This data is immediately outputted to the monitor T.V. 34 (Step 126). Subsequently, the second CPU operates the first motor 16a in the reverse or negative direction, thereby moving the probe 4 in the −X direction (Step 127) and makes a judgement as to whether the number of pulses obtained from the first encoder 18a has reached the value Xc obtained in step 103 (Step 128). When this number of the pulses has been reached, the second CPU stops the first motor 16a (Step 129). At the same time, the first CPU 32a sets the X coordinate value of the address in the image memory 32c by conducting Xa =Xa −1 (Step 130), and the A/D converter 28 outputs an image data signal only when it receives the trigger signal from the frequency divider 30 (Step 131). Then, the first CPU 32a writes the image data at the address (Xa, Ya) in the image memory 32c (Step 132), and the thus written data is immediately delivered to the monitor T.V. 34 (Step 133). Subsequently, a judgement is made as to whether the X coordinate value Xa of the address has become zero (Step 134) and, if not, the steps 130 to 134 are executed repeatedly, thus completing the pickup of the data.

Figure 7:
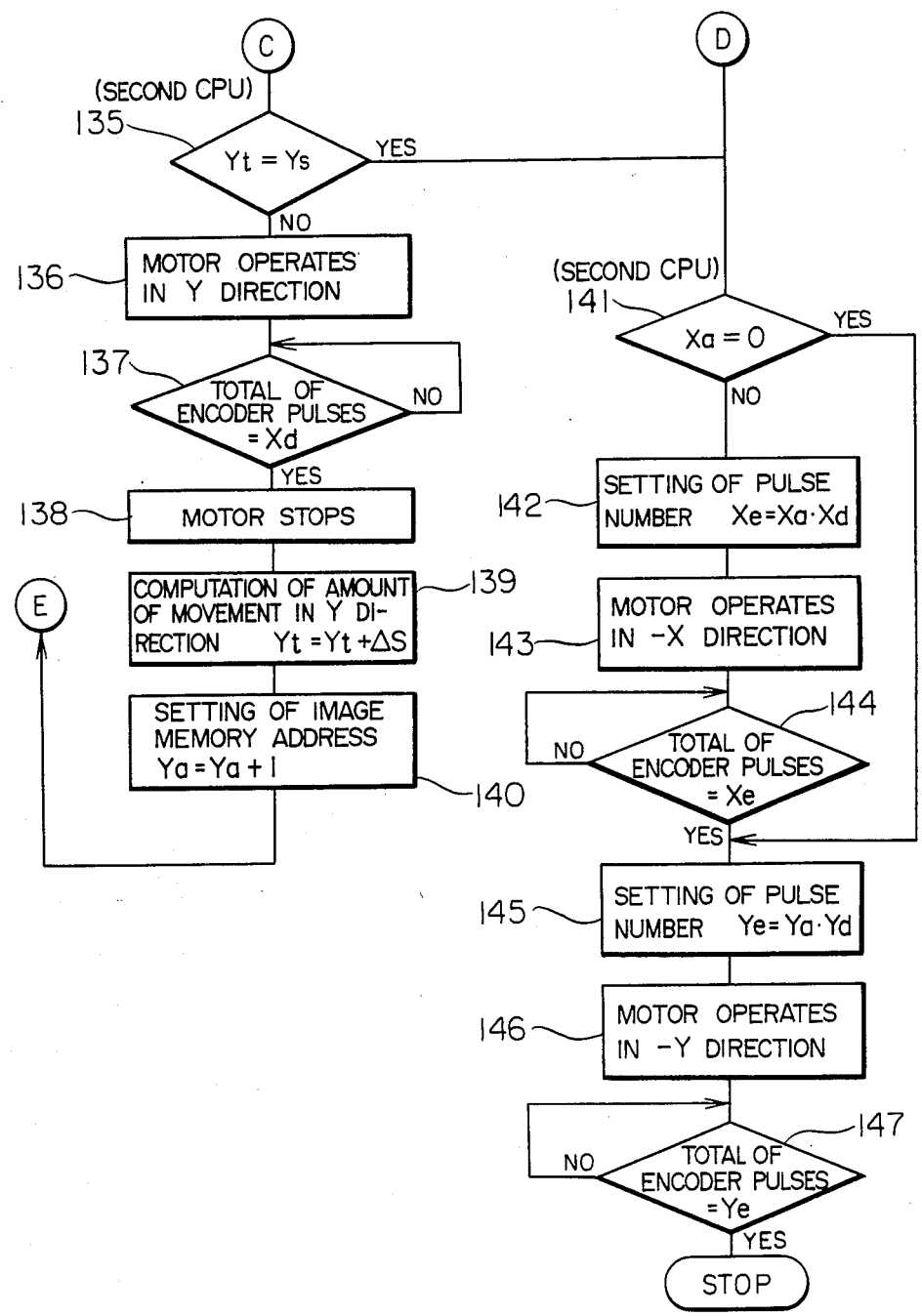

Subsequently, as shown in FIG. 7, the second CPU executes an operation similar to that of the steps 119 to 122 shown in FIG. 5, thereby causing the probe 4 by one pitch ΔS (Steps 135 to 138). Furthermore, the second CPU computes a movement in the Y direction by setting Yt=Yt+ΔS (Step 139) and sets the Y coordinate value of the address in the image memory 32c by conducting Ya=Ya+1 (Step 140). Then, the procedure returns to step 109 shown in FIG. 5, and the steps described hereinbefore are executed repeatedly.

When in step 119 or 135 a judgement is made that the movement Yt of the probe 4 in Y direction has reached the set distance Ys, a judgement is made in the second CPU as to whether the set X coordinate value Xa of the address in the image memory 32c has become zero (Step 141). If not, the second CPU computes Xe=Xa−Xd, thereby determining the number Xe of pulses of the first encoder 18a to provide a movement in Y direction necessary for returning the probe 4 to the initial position (Step 142). Then, the first motor 16a is operated in the negative direction, thereby causing the probe 4 to be moved in the −X direction (Step 143), and a judgement is made as to whether the total of the pulses outputted from the first encoder 18a has reached the set value Xe determined in step 142 (Step 144). When this value has been reached, the second CPU computes Ye=Ya·Xd, thus determining the number Ye of pulses of the second encoder 18b to provide a Y direction movement necessary for returning the probe 4 to the initial position (Step 145), and operates the second motor 16b in the negative direction, thereby causing the probe 4 to be moved in the −Y direction (Step 146). Then, a judgement is made as to whether the number of pulses from the second encoder 18b has reached the value Ye obtained in step 145 (Step 147). If this value has been reached, the second CPU operates to stop the second motor 16b. In the event that the judgement in step 141 has proved that the X coordinate value Xa of the address is zero, the procedure directly skips to the step 145, and executes the procedures in steps 145 to 147 in the same manner as that described above.

Figure 12:
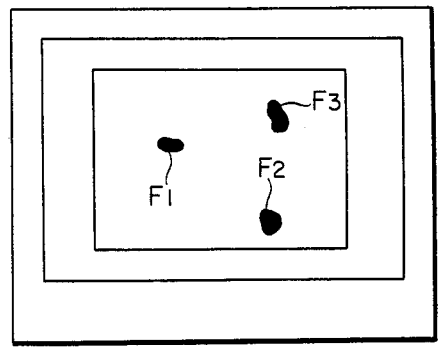
FIG. 12 is a view of a C-scope display on the screen of a monitor T.V. including a flaw information.

When the process described hereinbefore is completed, a C-scope display including, for example, the images of flaws $F_1$, $F_2$ and $F_3$ in the object D is obtained on the screen of the monitor T.V. 34 as shown in FIG. 12. If the data value carried by the digital signal obtained through the A/D converter 28 is binary-coded, a black-and-white C-scope display is obtained, whereas, when the digital signal is multi-coded, a black-and-white shaded or color C-scope display is obtained.

Function and Operation for A-Scope Display

Figure 8:
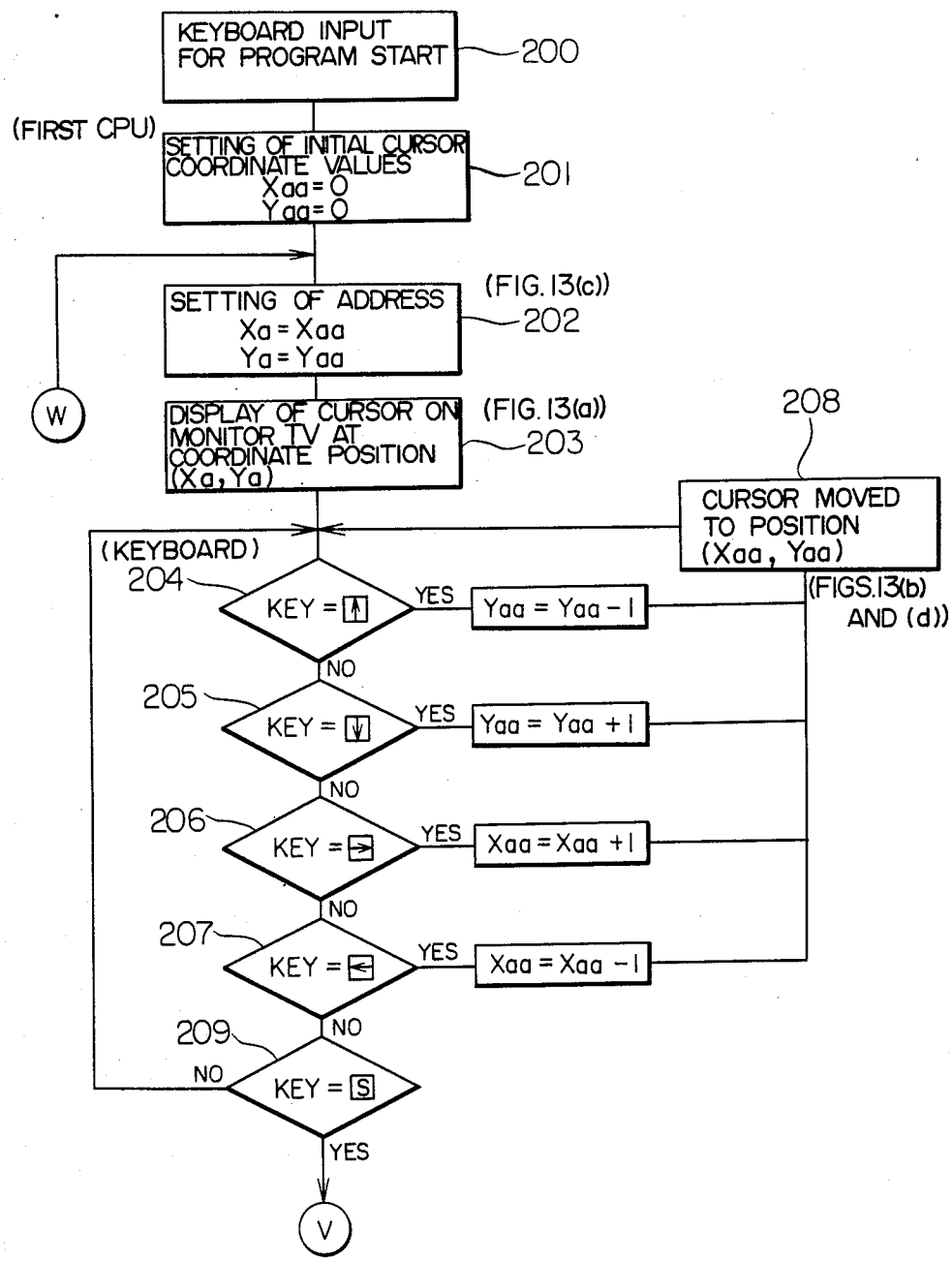
FIGS. 8 and 9 are flow charts showing procedures performed by the first and second CPUs to conduct A-scope display after the C-scope display.
Figure 9:
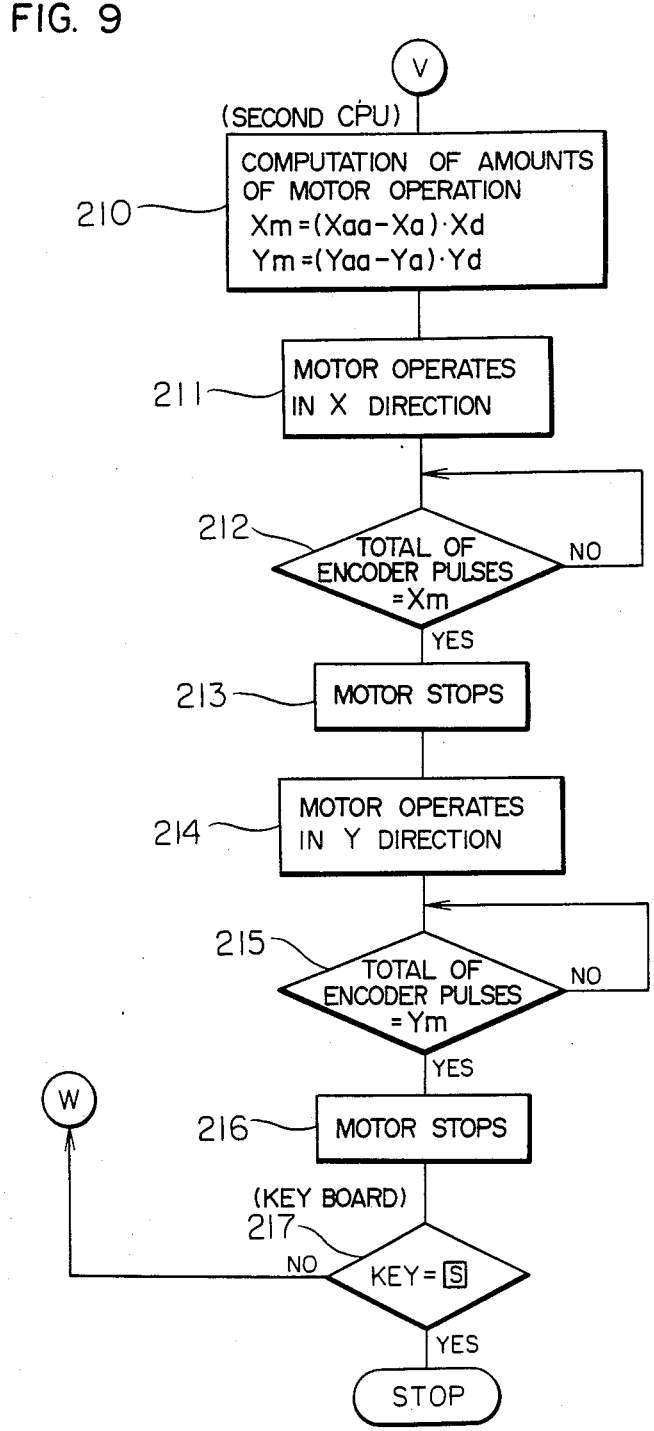
Figure 13:
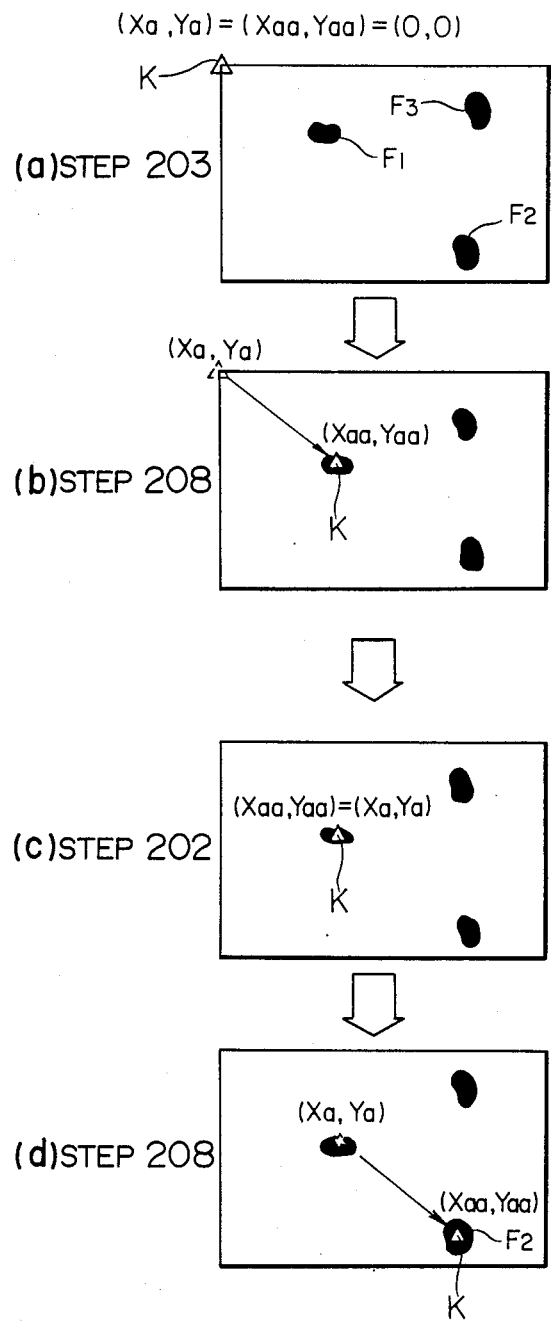
FIGS. 13a to 13d are views of the relationship between the movement of a cursor on the screen of a monitor T.V. and the address in an image memory.

Referring to FIG. 8 as the first step, the program for the A-scope display is started by operation of the keyboard 38 (Step 200). Then, the first CPU 32a operates to conduct the initial setting of the coordinate values Xaa, Yaa of the cursor on the screen of the monitor T.V. 34, by setting Xaa=0 and Yaa=0(Step 201). Subsequently, the address in the image memory 32c is set by conducting Xa=Xaa and Ya=Yaa (Step 202), so that the cursor K is displayed at a position on the screen of the monitor T.V. 34 corresponding to the address (Xa, Ya), as shown in FIG. 13a (Step 203). That is, the cursor K is displayed on the point of origin of the X - Y coordinate system as the coordinate values of the cursor have been initialized in Step 201. When it is desired to obtain an A-scope information concerning the flaw $F_1$ found in the C-scope display, the cursor K is moved to the position of the flaw $F_1$ on the screen by suitably operating cursor shifting keys on the keyboard 38, such as keys for shifting the cursor in Y, −Y, X and −X directions, while the screen of the monitor T.V. 34 is being watched, thereby changing the coordinate values (Xaa, Yaa) of the cursor K (Steps 204, 205, 206, 207). Then, the first CPU 32a accesses the address (Xaa, Yaa) in the image memory 32c corresponding to the coordinate values of the cursor (Step 208). The cursor K is thus located at the flaw $F_1$, as shown in FIG. 13b. After confirming that the cursor K is correctly located, a setting completion key on the keyboard 38 is depressed (Step 209). Then, as shown in FIG. 9, the second CPU computes Xm=(Xaa−Xa) Xd and Ym=(Yaa−Ya) Xd, thereby determining the numbers Xm and Ym of pulses of the first and the second encoders 18a, 18b to provide rotations of the first and the second motors 16a, 16b necessary for moving the probe 4 from the present position, i.e., the initial position to a position corresponding to the instant position of the cursor K (Step 210). Then, the first motor 16a is operated to move the probe 4 in the X direction (Step 211), and a judgement is made as to whether the total of the pulses from the first encoder 18a has reached the value Xm obtained in step 210 (Step 212). When this value is reached, the first motor 16a is stopped (Step 213). Similarly, the second motor 16b is operated to move the probe 4 in the Y direction (Step 214), and a judgement is made as to whether the total of the pulses from the second encoder 18b has reached the value Ym obtained in step 210 (Step 215). The second motor 16b is stopped when this value is reached (Step 216). As a result, the probe 4 is located at the position corresponding to the position of the cursor K on the screen of the monitor T.V., i.e., at the position right above the flaw $F_1$ in the object D. Then, the probe 4 is energized to emit a supersonic wave, so that A-scope display of the flaw $F_1$ is obtained on the oscilloscope 24 as shown in FIG. 2b. Thus, using this A-scope display, it is possible to obtain necessary flaw information such as depth and size of the flaw $F_1$.

When it is desired to obtain the A-scope display of the flaw $F_2$ found in the C-scope display, the program start key on the keyboard 38 is depressed again (Step 217), so that the process returns again to step 202 to renew the setting of the address in the image memory 32c by setting Xa=Xaa and Ya=Yaa (Step 202), thereby displaying the cursor K at the position on the screen of the monitor T.V. 34 corresponding to the address (Xa, Ya), as shown in FIG. 13c (Step 203). Namely, the position of the cursor on the screen is not but the point of origin of the coordinate system is moved to the position corresponding to the address (Xaa, Yaa). Then, as explained before, necessary keys on the keyboard 38 are operated to change the coordinate values (Xaa, Yaa) of the cursor K so that the cursor K may be moved to the position of the flaw $F_2$ (Steps 204 to 207), thus setting the cursor address in the image memory 32c as the address (Xaa, Yaa) (Step 208), as shown in FIG. 13d. Then, the cursor setting completion key is depressed, so that the procedures in steps 210 to 216 are repeatedly conducted and the probe 4 is moved directly from the position corresponding to the flaw $F_1$ to the position corresponding to the flaw $F_2$ without being returned to the initial position. Thus, as the probe 4 is energized to emit a supersonic wave, A-scope display of the flaw $F_2$ is obtained on the oscilloscope 24. The A-scope display data can be obtained in the same way also concerning the flaw $F_3$ found in the C-scope display. It will thus be seen that required number of A-scope display data can be successively obtained in a short time and with ease, using the data obtained from the single C-scope display.

Namely, according to the described embodiment, the flaw data over the entire portion of the object D can be roughly learned by a single C-scope display, and using this data, the probe 4 can be automatically located at positions right above the flaws in the object D by moving the cursor on the monitor T.V. screen to the positions of the flaws, so that by conducting A-scope display at those positions, it is possible to obtain the detailed data of each flaw such as depth and size thereof. This operation can be conducted very simply and in a very short time.

The described embodiment permits a free setting of the range of scanning of the probe by the operation of the keyboard 38. However, in the case where the flaw detecting system is intended for exclusive use in the inspection of a specific object, the scanning range can be determined beforehand as a fixed one. In such a case, it is advisable to compute beforehand the data pickup pitch ΔS by dividing the X direction distance or length of the scanning range by the number of the X coordinate values of the addresses in the image memory 32c, i.e., by 250, and to set the thus obtained pitch ΔS in the first CPU 32a as a fixed value. In this case, needless to say, the operation of the keyboard 38 for setting the scanning range upon initiation of flaw detection operation is eliminated, so that the process can start directly from step 106 in the flow chart shown in FIG. 4. In this case also, what is important is to determine the data pickup pitch ΔS such that the number of the data pickups in each movement of the probe in X direction coincides with the number of X coordinate values of the addresses in the memory 32c, i.e., 250, and the pitch ΔS becomes the same as the value obtained by dividing the X direction distance of the scanning range by that number, i.e., 250.

In the described embodiment, the single probe 4 has both the functions to emit a supersonic wave and receive a reflected wave. This, however, is not exclusive and the arrangement may be such that a pair of probes are arranged across the object D so that one of the probes function to emit a supersonic wave and the other functions to receive the supersonic wave transmitted through the object D whereby the same effect can be achieved as that offered by the described embodiment.

The arrangement in the described embodiment for delivering a trigger signal from the frequency divider 30 into the A/D converter 28 for effecting the A/D conversion may be modified in such a manner that the trigger signal is delivered to the CPU 32a while the A/D converter always outputs the image data signal, so that the first CPU 32a writes the image data at the addresses in the image memory only when the CPU 32a receives the trigger signal from the frequency divider 30. It is also possible to omit the frequency divider 30, provided that the first CPU 32a may function to observe the number of pulses from the first encoder 18a and to deliver the trigger signal to the A/D converter 28 at each pitch obtained by computation, or to directly write the image data always supplied from the A/D converter 28 at the addresses in the image memory 32c at the pitch, without generating any trigger signal.

In the described embodiment, the pitch ΔS of data pickup operations is determined as a distance value, by dividing the X direction distance of the scanning range by the previously set number of data pickups during each movement in X direction over the scanning range. This, however, is not exclusive and the pitch ΔS can be determined as a time value, by computing the time required for one X direction movement of the probe based on the X direction distance of the scanning range and the speed of the first motor 16a, and dividing the thus computed time by the number of the data pickups.

The use of the cursor as a position indicator for indicating the position of the flaw image on the C-scope display is not exclusive, and the position may be indicated by other position indicator such as a touch panel. In this case, a transparent touch panel is adhered on the screen of the monitor T.V. 34 and the flaw image on the display is touched through the touch panel, so that the touch panel produces voltages proportional to the X and Y coordinate values of the touched position and delivers signals of digital values corresponding to these voltages. These digital signals can be used for accessing the address in the image memory 32c corresponding to the touched position, i.e., the position of the flaw.

In the described embodiment, the gate width in the gate circuit 26 is extended as much as possible in the thicknesswise direction of the object D. As mentioned before, in the case the depth of the portion to be inspected is specified, as in the case of inspection of the bonding between adjacent layers in a semiconductor, the gate width can be narrowed to cover only the specified depth portion which is in this case the bonding layer, and in this case, a clear C-scope display can be obtained by moving the probe 4 in the Z direction perpendicular to both the X and Y directions to adjust the focus of the probe 4. The C-scope display alone, however, cannot provide exact information concerning the delicate state of separation in the bonding interface, even though the image is clear. According to the invention, this delicate state can be confirmed and the presence of any separation can be detected without fail by the A-scope display which follows the C-scope display, since the phase of waveform of the flaw echo is inverted in the A-scope display when such a separation exists.

The described embodiment employs such a flaw detection pattern that a C-scope display is followed by A-scope display. This pattern, however, is only illustrative and the invention does not exclude the use of other patterns. For instance, in a modification, after A-scope display which follows C-scope display is conducted, water distance can be adjusted so as to cause the supersonic wave from the probe 4 to be focused on the depth of a flaw which can be learn from the A-scope data and then a second C-scope display can be conducted under such adjustment, thereby permitting a clear C-scope display of the flaw and, hence, detailed data of the flaw to be obtained.

As has been described, the supersonic flaw detecting system according to the invention is adapted to write the image data at the corresponding address in the image memory at each pitch which has been determined such that the number of data pickups during the relative movement between the probe and the object coincides with the number of the corresponding addresses in the image memory means, to thereby cause C-scope display of the image data to be effected. The supersonic flaw detector of the invention is also adapted to compute, when the position indicator is displayed on the screen of the monitor T.V., the amount of operation of the scanning device necessary for locating the probe relative to the object at a position corresponding to the position indicator on the screen, from the pitch and the accessed address, and operate the scanning device by the thus computed amount to locate the probe at the corresponding position, thereby permitting A-scope display to be effected at such a position. It is, therefore, possible to check the object for any flaw and to obtain detailed data of the flaw such as depth and size of the flaw, in a very short time and without difficulty.

What is claimed is:

1. A supersonic flaw detecting system having a probe that emits a supersonic wave towards an object to be inspected, scanning means for causing a relative movement between said probe and said object in two orthogonal directions, a pulser-receiver that supplys pulses to said probe and receive the supersonic wave from said object and produce an electric signal indicative thereof, signal processing means for converting said electric signal from said pulser-receiver into an image data signal for a C-scope display, oscilloscope means for conducting an A-scope display of said electric signal from said pulser-receiver, and a monitor T.V. having a screen for displaying the C-scope display of said image data signal from said signal processing means, said supersonic flaw detector further comprising:

image memory means connected to said monitor T.V. and having addresses corresponding to the coordinate values of a coordinate system assumed on the screen of said monitor T.V.;

operation means for being operated by an operator and including position indicating means for allowing the operator to designate a desired position on the screen of said monitor T.V.; and control means connected to said scanning means, said signal processing means, said image memory means and said operation means, and including:

first means for writing, when said probe and object are relatively moved by said scanning means, the image data carried by said image data signal from said signal processing means in the image memory means at a corresponding address thereof at each pitch determined such that the number of data pickups during the relative movement between said probe and object coincides with the number of the corresponding addresses in said image memory means, to thereby provide data for C-scope display of the image data to be produced on the screen of said monitor T.V.;

second means for allowing access to one of the addresses in said image memory means corresponding to said desired position on the screen designated by operation of said position indicating means, and third means for computing, when said one of the addresses in said image memory means is accessed by the operation of said position indicating means, the amount of drive of said scanning means necessary for moving said probe relative to said object to a position corresponding to the designated position on the screen of the monitor T.V. from data on said pitch and said accessed address in said image memory means and driving said scanning means until said computed amount of drive is reached whereby said probe is automatically moved to and located at said position corresponding to the designated position on the screen of said monitor T.V. for allowing A-scope display at such a position to be successively followed.

2. A supersonic flaw detecting system according to claim 1, wherein said control means further provides the function of allowing the scanning range of said probe relative to said to be set by an operation of said operation means and stores beforehand a number of data pickups which coincides with the number of the corresponding addresses in said image memory means for computing said pitch from said number of data pickups and said scanning range as set.

3. A supersonic flaw detecting system according to claim 2, wherein said control means further function to compute, when the relative movement between said probe and said object caused by said scanning means is completed, the amount of drive of said scanning means necessary for returning said probe to an initial position for the probe, from said pitch and the address in said image memory means in which the last image data has been written, and driving said scanning means until the thus computed amount of drive is reached whereby said probe is automatically returned to said initial position.

4. A supersonic flaw detecting system according to any one of claims 1, 2 and 3, further comprising data pickup timing means connected to said scanning means, control means and said signal processing means for instructing said signal processing means to output said image data signal at the timing of each said pitch.

5. A supersonic flaw detecting system according to claim 4, wherein said scanning means includes a first motor and a second motor for effecting the relative movement in one and the other of two orthogonal directions, respectively, and a first encoder and a second encoder connected to said first motor and said second motor, respectively, for producing pulse signals of the same pulse width in proportion in number to the amounts of rotation of the respective motors; said data pickup timing means includes a frequency divider connected between said first encoder and said signal processing means for demultiplying said pulse signals from said first encoder and delivering trigger signals to said signal processing means at timings obtained as a result of the demultiplication; and said control means further functions to divide said pitch by the pulse width of said pulse signal from first encoder to compute a number of demultiplication, and instructs said frequency divider to effect the demultiplication by the thus computed number.

6. A supersonic flaw detecting system according to claim 5, wherein said control means further functions to divide X direction distance of the set scanning range by the pulse width of said encoder pulse signal to compute a number of pulses of said first encoder necessary for effecting the relative movement by said set distance in X direction and driving said first motor until said pulse number is counted; for dividing Y direction distance of the set scanning range by said pitch to compute a data sample number necessary for covering the Y direction distance of said set scanning range and driving said first motor such that the relative movements in the X direction and in the -X direction are alternatingly repeated until said data sample number is counted; and for driving, each time the relative movement in the X or the -X direction is completed, said second motor to effect the relative movement in the Y direction until the number of the encoder pulses coinciding with the number of demultiplication are counted, and thereafter initiating the next movement in the -X or the X direction.

7. A supersonic flaw detecting system according to claim 5, wherein said third means in said control means is programmed to multiply the X coordinate value and the Y coordinate value of the address in said image memory means set by said position indicating means with said number of demultiplication to compute numbers of pulses to be provided to said first and second encoders necessary for locating said probe at the position corresponding to the position of said position indicating means on the T.V. screen to thereby determine the amount of drive of said scanning means necessary for automatically locating said probe at said last-mentioned position for said A-scope display.

8. A supersonic flaw detecting system according to claim 5, wherein said control means multiplies the X coordinate value and the Y coordinate value of said address in said image memory means in which the last image data is written with said number of demultiplication to compute the numbers of pulses of said first and second encoders necessary for returning said probe to said initial position to thereby determine the amount of drive of said scanning means necessary for automatically returning said probe to said initial position.

* * * * *